United States Patent [19]

Warren et al.

[11] Patent Number: 5,693,481

[45] Date of Patent: Dec. 2, 1997

[54] INHIBITOR OF CYTOKINE ACTIVITY AND APPLICATIONS THEREOF

[75] Inventors: Mary Kim Warren, Rockville, Md.; Robert Drummund, Richmond; Leah B. Conroy, San Francisco, both of Calif.

[73] Assignee: Chiron Corporation, Emeryville, Calif.

[21] Appl. No.: 465,133

[22] Filed: Jun. 5, 1995

Related U.S. Application Data

[60] Division of Ser. No. 494,624, Mar. 16, 1990, which is a continuation-in-part of Ser. No. 480,248, Feb. 15, 1990, abandoned.

[51] Int. Cl.$^6$ .................. C12Q 1/02; C12P 1/00; G01N 33/574; C12N 5/00
[52] U.S. Cl. .................. 435/29; 435/41; 435/7.1; 435/7.21; 435/7.23; 435/240.2; 436/63; 436/74; 530/351; 530/412; 530/413; 530/416
[58] Field of Search .................. 435/29, 7.1, 7.21, 435/7.23, 41, 240.2; 436/63, 74; 530/351, 412, 413, 416

[56] References Cited

U.S. PATENT DOCUMENTS

| | | | |
|---|---|---|---|
| 4,411,993 | 10/1983 | Gillis | 435/29 |
| 4,473,493 | 9/1984 | Gillis | 435/29 |
| 4,778,879 | 10/1988 | Mertelsmann et al. | 530/351 |
| 4,789,658 | 12/1988 | Yoshimoto et al. | 514/12 |
| 4,798,886 | 1/1989 | Kato et al. | 530/416 |
| 4,973,577 | 11/1990 | Vale, Jr. et al. | 514/12 |
| 5,422,425 | 6/1995 | Kriegler et al. | 530/324 |
| 5,527,546 | 6/1996 | Penza et al. | 424/573 |

FOREIGN PATENT DOCUMENTS 9112334  8/1991  WIPO.

OTHER PUBLICATIONS

Larrick, James W.; "Immunology Today", vol. 10, No. 2, 1989 (Native interleukin 1 inhibitors). (Month not available).

Davis et al, "Microbiology" 4th Edition, pp. 240, 339–340, 1990. (Month not available).

*Primary Examiner*—Louise Leary
*Attorney, Agent, or Firm*—Donald J. Pochopien; Paul B. Savereide; Robert P. Blackburn

[57] ABSTRACT

Described herein are compositions that have prophylactic or therapeutic applications for disease resulting from the production of cytokines, and preferably the cytokine IL-6, wherein the compositions consist of activin like molecules.

11 Claims, 10 Drawing Sheets

INHIBITOR OF CYTOKINE ACTIVITY AND APPLICATIONS THEREOF

This application is a division of U.S. Ser. No. 07/494,624, filed Mar. 16, 1990, now pending, which is a continuation-in-part of U.S. Ser. No. 07/480,248, filed Feb. 15, 1990, now abandoned.

FIELD OF THE INVENTION

This invention is in the field of immunology/biochemistry. Described herein are compositions that have prophylactic or therapeutic applications for the treatment of diseases resulting from the production of cytokines. More specifically, an inhibitory material, having the properties of activin, is shown that effects the biological activity of the cytokine, interleukin-6 (IL-6).

BACKGROUND OF THE INVENTION

Cytokines are small molecular weight proteins that have a myriad of biological functions. For example, cytokines are known to be capable of stimulating their own synthesis, as well as the production of other cytokines from a variety of cell types. They are also associated with disease. A good example is the presence of the cytokines interleukin-1 (IL-1) and tumor necrosis factor (TNF) that alone or in combination cause a shock state in animals that hemodynamically and hematologically is characteristic of septic shock in man caused by bacterial infection. Also, TNF, in addition to playing a critical role in sepsis, has recently been shown to be involved in initiating the expression of human immunodeficiency virus in human cells that carry latent virus. Folks et al., 1989, *Proc. Natl. Acad. Sci. USA*, 86:2365. Thus, preventing or inhibiting the formation of the 17 kD, or lower molecular weight forms of TNF would be a valuable prophylactic for the treatment of AIDS patients by preventing the expression of virus that is latent in the patient. TNF and IL-1 also play a role in various autoimmune diseases, particularly arthritis. Duff, et al., 1987, *International Conference on Tumor Necrosis Factor and Related Cytotoxins*, 175:10.

It is thus becoming apparent that aside from their normal biological functions, which have not been fully elucidated, that cytokines are associated with systemic changes arising from infection and tissue injury.

In addition to IL-1 and TNF, another cytokine, IL-6, also termed hybridoma growth factor, interferon-beta-2, B-cell stimulatory factor 2, 26 kilodalton protein, and hepatocyte stimulating factor, is involved in infection, particularly sepsis, as well as in affecting the growth of tumor cells. Indeed, Hack, et al., 1989, *Blood*, 74:1704, have shown that a significant number of patients with sepsis display increased plasma levels of IL-6, and that the amount of IL-6 correlates with the symptoms of shock and with clinical prognosis. In the sepsis patients shown in that report, serum IL-6 levels were on the order of 1,000 U/ml.

Although the precise pathology of bacteremia is not completely elucidated, it is believed that bacterial endotoxins, lipopolysaccharides (LPS), are the primary causative agents. LPS consist of at least three significant antigenic regions, the lipid A, core polysaccharide, and O-specific polysaccharide. The latter is also referred to as O-specific chain or simply O-antigen. The O-specific chain region is a long-chain polysaccharide built up from repeating polysaccharide units. The number of polysaccharide units differ among different bacterial species and may vary from one to as many as six or seven monosaccharide units. While the O-specific chain varies among different gram-negative bacteria, the lipid A and core polysaccharides are similar if not identical.

IL-6 acts on a variety of cells including lymphocytes, hepatocytes (causing the production of acute phase protein synthesis) hematopoietic stem cells and nerve cells. It may act as either a growth factor, a growth inhibitor, or even a differentiation inducing factor. Kishimoto, T. and Hirano, T., 1988, *Annual Review of Immunology*, 6:485–512. It has recently been suggested that IL-6 is an autocrine growth factor for renal cell carcinomas. Miki, S., et al., 1989, *FEBS*, 250:607–610. Thus, compounds that interfere with the autocrine activity of IL-6 may be effective chemotherapeutics.

Native IL-6 has a molecular weight of 19–30 kD and an immunoreactive species of 60–70 kD has also been reported (see Kelfgott, et al., 1989, *J. Immunol.*, 142:948 and Jablon, et al., 1989, *J. Immunol.*, 142:1542). The gene coding for a human IL-6 polypeptide has been cloned and expressed as shown by the following European patent applications: EPA 0 220 574, published May 6, 1987, to Revel, M, et al., entitled "Human interferon beta2A and interferon-beta2B, vectors containing genes coding for said interferons, cell lines producing same and use of said interferons as pharmaceuticals"; EPA 0 254 399, published Jan. 27, 1988, to Clevenger, W., et al., entitled "B-cell stimulating factor"; EPA 0 257 406, published Mar. 2, 1988, to Kishimoto, T., et al., entitled "Recombinant B-cell differentiation factor"; EPA 0 261 625, published Mar. 30, 1988, to Honjo, T., et al., entitled "Human B-cell differentiation factor and process of producing said factor"; EPA 0 267 779, published May 18, 1988, entitled "Human pleiotropic immune factor and muteins thereof"; and PCT WO 88/00206, published Jan. 14, 1988, to Clark, S., et al., entitled "Production and use of IL-6".

As mentioned above, IL-6 has been cloned from a number of animal species, including human and mouse. Human IL-6 consist of 184 amino acids with 4 cysteine residues. Hirano, T. et al., 1986, *Nature*, 324:73. Human IL-6 cDNA shares a good deal of homology with murine IL-6 cDNA. Indeed, at the DNA level human IL-6 shows a 65% homology with murine IL-6, and at the protein level there is 42% homology. The position of the 4 cysteine residues is conserved. Curiously, the sequence of IL-6 is significantly homologous to G-CSF. In addition, the position of the 4 cysteine residues of IL-6 match those of G-CSF. This suggests a common functional similarity between the two molecules, as well as their possible origin from a common ancestor gene.

No doubt cytokines will be found to play a role in diseases other than those mentioned above. Nevertheless, the importance of cytokines in disease, particularly sepsis, is readily apparent when the extent of the disease is considered. In the United States alone nosocomial bacteremia develops in about 194,000 patients, and of these about 75,000 die. Maki, D. G., 1981, *Nosocomial Infect.*, (Dikson, R. E., Ed.), page 183, Yrke Medical Books, U.S.A. Most of these deaths are attributable to six major gram-negative bacilli, and these are *Pseudomonas aeruginosa, Escherichia coli,* Proteus, Klebsiella, Enterobacter and Serratia. The current treatment for bacteremia is the administration of antibiotics which, unfortunately, have limited effectiveness. Thus, it will be appreciated that there is an ongoing clinical need for medicaments that can be used by the physician to regulate the affects of cytokine production.

SUMMARY OF THE INVENTION

One aspect of the invention described herein consists of a protein inhibitor of cytokine activity that has applications for the therapeutic or prophylactic treatment of disease, preferably diseases involving IL-6. Herein after the inhibitory molecule may alternatively be referred to as an inhibitor of cytokine activity, or cytokine inhibitor. By way of example, the activity of the inhibitor is demonstrated against IL-6 activity, without intending to suggest how the protein exerts its affect. That is, by directly or indirectly interfering with the activity of IL-6. It is to be anticipated that by indirectly interfering with IL-6 activity that the inhibitor would be interfering with the activity of other cytokines. Thus, in this sense the protein inhibitor described herein is an inhibitor of cytokine activity generally.

A second aspect of the invention is the description of a dimeric proteinaceous inhibitor of cytokine activity that is secreted by transformed melanoma cells and that has an apparent subunit molecular weight of about 15–16.4 kilodaltons as determined by sodium dodecyl sulphate polyacrylamide gel electrophoresis (SDS-PAGE).

A third aspect of the invention is the description of a dimeric proteinaceous inhibitor of cytokine activity that is produced by malignant melanoma cells and which production is enhanced by IL-1.

A fourth aspect of the invention are methods for purifying an inhibitor of cytokine activity using ion exchange and sizing chromatography.

A fifth aspect of the invention is the description of native or recombinant molecules that exhibit inhibitory activity and consists of activins.

A further aspect of the invention is a description of methods whereby an inhibitor of cytokine activity is used to beneficially treat patients, either prophylactically or therapeutically, that suffer from a variety of immunologically responsive diseases including sepsis.

BRIEF DESCRIPTION OF THE DRAWINGS

Table 1 shows various cell lines tested for the production of the cytokine inhibitor by inhibiting IL-6 activity.

Table 2 shows the effect of trypsin on cytokine inhibitor activity.

Table 3 shows that the cytokine inhibitor competes with IL-6 as revealed by the reversal of IL-6 inhibitor inhibition of IL-6 stimulation of B9 cell growth at elevated concentrations of IL-6.

DETAILED DESCRIPTION OF THE INVENTION

The invention described herein draws on previously published work and pending patent applications. By way of example, such work consists of scientific papers, patents or pending patent applications. All of these publications and applications, cited previously or below are hereby incorporated by reference.

In its primary aspect, the present invention concerns the isolation and identification of a particular factor hereinafter referred to as cytokine inhibitor factor, or simply, inhibitor. This inhibitor has been shown to be constitutively produced in human malignant melanoma cells, preferably the cell line denoted A375, which is on deposit with the American Type Culture Collection and has Accession No. 1619. The cytokine inhibitor has been characterized with respect to certain of its molecular and chemical properties, as well as its ability to inhibit the activity of the cytokine, IL-6. Each of these will be discussed separately below.

Before discussing the subject invention cytokine inhibitor, it is important to be aware that the inhibitor described herein consists of proteinaceous material having a defined chemical structure. However, the precise structure of the inhibitor depends on a number of factors, particularly chemical modifications known to occur to proteins. For example, since all proteins contain ionizable amino and carboxyl groups it is, of course, apparent that the inhibitor may be obtained in acidic or basic salt form, or in neutral form. It is further apparent, that the primary amino acid sequence may be augmented by derivatization using sugar molecules (glycosylation) or by other chemical derivatizations involving covalent, or ionic attachment to the inhibitor with, for example, lipids, phosphate, acetyl groups and the like, often occurring through association with saccharides. These modifications may occur in vitro, or in vivo, the latter being performed by a host cell through post-translational processing systems. It will be understood that such modifications, regardless of how they occur, are intended to come within the definition of the cytokine inhibitor so long as the activity of the protein, as defined below, is not destroyed. It is to be expected, of course, that such modifications may quantitatively or qualitatively increase or decrease the biological activity of the molecule, and such chemically modified molecules are also intended to come within the scope of the invention.

I. Identification of Cytokine Inhibitor

Cell lines may be used as a source of the cytokine inhibitor; however, it should be understood that tissues or organs may also be sources of the inhibitor and may be conveniently assayed for inhibitor activity using known assays. Furthermore, as discussed in detail below, the inhibitor has an amino acid sequence that is substantially similar to the $\beta_A$ chain polypeptide present in several proteins that are known in the art, and thus these proteins would have the biological activity ascribable to the inhibitor. A comparison of the amino acid sequence of the IL-6 inhibitor to sequences of known proteins in a computerized protein data base revealed that the inhibitor has the amino terminal sequence of the $\beta_A$ chain of at least two proteins and includes inhibin A, and activin. Both molecules consists of an A and β chain. The β chains have substantial homology and this is relevant to the instant invention since they would have similar biological activity.

There are two forms of inhibin, Inhibin A and Inhibin B. Both consist of two polypeptide chains, an A and β chain, with approximate molecular weights of 43 kD and 15 kD, respectively. PCT International Application Number: PCT/AU86/00097, inventor Forage, R., et al. The B chains of Inhibin A and Inhibin B, $\beta_A$ and $\beta_B$ respectively, are distinguishable by differences in the amino terminus. The IL-6 inhibitor described herein has an amino terminal sequence substantially identical to the $\beta_A$ chain of Inhibin A. The amino acid sequence of the β chain of Inhibin A is shown below.

```
1                                          10
Gly Leu Glu Cys Asp Gly Lys Val Asn Ile Cys Cys Lys Lys
                    20
Gln Phe Phe Val Ser Phe Lys Asp Ile Gly Trp Asn Asp Trp
                    35                40
Ile Ile Ala Pro Ser Gly Tyr His Ala Asn Tyr Cys Glu Gly
                         50                55
Glu Cys Pro Ser His Ile Ala Gly Thr Ser Gly Ser Ser Leu
                                          70
Ser Phe His Ser Thr Val Ile Asn His Tyr Arg Met Arg Gly
                              80
His Ser Pro Phe Ala Asn Leu Lys Ser Cys Cys Val Pro Thr
                    90
Lys Leu Arg Pro Met Ser Met Leu Tyr Tyr Asp Asp Gly Gln
     100                 115
Asn Ile Ile Lys Lys Asp Ile Gln Asn Met Ile Val Glu Glu
     115
Cys Gly Cys Ser.
```

Activin, also known as follicle-stimulating hormone releasing protein, is a 28 kD dimeric protein consisting of two $\beta_A$ chain polypeptides, each with molecular weights of about 14 kD, covalently attached by a disulfide bond.

As discussed more in detail below, the IL-6 inhibitor of the instant invention consists of a dimeric proteinaceous material as revealed by reducing and non-reducing SDS-PAGE. The similarities in the amino terminal amino acid sequence, of the instant IL-6 inhibitor and activin, and the similar molecular weights of the two molecules, suggest that the instant inhibitor is substantially similar to activin. This further suggests that activin would exhibit those properties described herein that are characteristic of the IL-6 inhibitor.

Two preferred assays for demonstrating the biological activity of the inhibitor are described below: inhibition of B9 cell IL-6 dependent growth, or inhibition of IL-6 dependent release of haptoglobin by cells of liver origin, preferably the hepatoma cell line, HepG2.

Several cell lines were tested to determine if they produce the inhibitor. Table 1 shows the cell lines tested, and the results. Each of the cell lines shown in Table 1 was grown in a suitable cell culture media, preferably ISCOVES media supplemented with 10% fetal calf serum. Conditioned media may be prepared using a number of media, and the preferred media is serum free RPMI containing glutamine. Cells were kept in RPMI medium for a defined period of time and the medium assayed for inhibitor activity in either the B9 cell assay or the haptoglobin assay mentioned above. It is apparent from a review of Table 1 that the human malignant melanoma cell line, A375, shows significant production of the cytokine inhibitor material. A375 is described in detail by Nakai, et al., 1988, *Biochemical & Biophysical Res. Comm.*, 154(3):1189.

TABLE 1

| Cell Lines Tested | IL-6 Inhibitor |
|---|---|
| A375 | + |
| MEL-28 | – |
| Hs294T | – |
| LD-1 | – |
| MEL-3 | – |
| KB-1 | – |

The cytokine inhibitor was initially identified in A375 conditioned media by its ability to inhibit IL-6-induced haptoglobin release from HepG2 cells using the assay described by Castell, 1989, *FEBS*, 242(2):237. The precise format of the assay may vary, but the preferred assay is an enzyme linked immunosorbent assay (ELISA) for haptoglobin. It is described in detail in the Examples. The ELISA procedure is known in the art and is described by Engvall, E., 1977, *Med. Biol.*, 55:193. Briefly, the presence of haptoglobin in the conditioned media is determined using antibody to haptoglobin. The procedure consists of coating flat-bottom 96 well microtitre plates with antibody to haptoglobin, adding the conditioned media sought to be assayed for haptoglobin, and detecting the presence of antibody bound haptoglobin using a second antibody. The second antibody may be labelled with an appropriate reporter molecule and detected directly, or a third labelled antibody can be employed which binds to and reveals the second antibody. Needless to say, the antibodies should be selected so that there is little or no cross reactivity during the assay which would interfere with the detection of haptoglobin.

As discussed above, the assay of the present invention employs a labelled antibody. The label can be any type that allows for the detection of the antibody. Generally, the label directly or indirectly results in a signal which is measurable and related to the amount of label present in the sample. For example, directly measurable labels can include radio-labels (e.g. 125I, 35S, 14C, etc.). A preferred directly measurable label is an enzyme, conjugated to the antibody, which produces a color reaction in the presence of the appropriate substrate. (e.g. horseradish peroxidase/o-phenylenediamine). An example of an indirectly measurable label is antibody that has been biotinylated. The presence of this label is measured by contacting it with a solution containing a labeled avidin complex, whereby the avidin becomes bound to the biotinylated antibody. The label associated with the avidin is then measured. A preferred example of an indirect label is the avidin/biotin system employing an enzyme conjugated to avidin, the enzyme producing a color reaction as described above.

Which ever label is selected, it results in a signal which can be measured and is related to the amount of label in a sample. Common signals are radiation levels (when radioisotopes are used), optical density (e.g. when enzyme color reactions are used) and fluorescence (when fluorescent compounds are used). It is preferred to employ a nonradioactive signal, such as optical density (or color intensity) produced by an enzyme reaction. Numerous enzyme/substrate combinations are known in the immunoassay an which can produce a suitable signal. See, e.g., U.S. Pat. Nos. 4,323,647 and 4,190,496, the disclosures of which are incorporated herein.

Additionally, haptoglobin can be further characterized by immunoblot analysis and immunofluorescence assay. Immunoblot analysis can be carried out as described by Trobwin, H. et al., 1979, *PNAS USA*, 76:4350 and Burnette, W., 1981, *Analytical Biochem.*, 112:195. The methods for performing immunofluorescence are also known in the art.

B9 is a murine hybridoma cell line that exhibits IL-6 dependent growth. Using this assay, which is also described in the Examples, and shown by Helle et al., 1988, *Eur. J. Immunol.*, 18;1535, the presence of cytokine inhibitor activity in A375 conditioned media was confirmed. The assay consisted of growing the cells in a suitable cell culture media supplemented with fetal calf serum, $5 \times 10^{-5}$M 2-mercaptoethanol, and other supplements known in the art, and varying amounts of IL-6. None of the cell lines, with the exception of A375, inhibited the IL-6 induced growth of the B9 cells.

A key aspect of the inhibitor obtained from A375 cells is that its production is significantly stimulated by another cytokine, IL-1. This was confirmed using the B9 proliferation assay, described above.

II. Purification of Cytokine Inhibitor

A variety of purification methods may be drawn on to purify the inhibitor. Regardless of the procedure chosen, and depending on the nature of the biological material that the inhibitor is purified from, it may be desirable to have present in the various purification solutions one or more protease inhibitors, such as, for example, PMSF. Furthermore, as is known in the art, certain of the purification steps may be conducted at temperatures that reduce the risk of the inhibitor being proteolyzed. Furthermore, to increase the yield of cytokine inhibitor obtainable from a particular purification scheme, A375 cells were grown and induced to produce the inhibitor in elevated amounts using IL-1, as described in the Examples.

Preferably the purification procedure will employ at least one ion exchange chromatographic step. More preferred is anion exchange chromatography coupled with additional purification steps. A number of anion exchange chromatographic materials can be employed, DEAE-Sepharose, obtainable from Pharmacia Corporation, is preferred, partly because the cytokine inhibitor is readily recoverable therefrom in good yield using standard biochemical anion exchange techniques. For example, if DEAE-Sepharose is employed as the initial chromatographic step, approximately 40 µg of the inhibitor can be obtained from 4 liters of A375 conditioned media. As mentioned above, the initial sequence of chromatographic procedures is not rigid, and can be varied. In addition to anion exchange chromatography, other chromatographic methods may be employed, alone or in combination, which are known and practiced in the art. Exemplary methods would include affinity chromatography using, preferably, antibodies specific for the inhibitor.

The methods for eluting proteins from anion exchangers, and affinity columns are generally documented in the literature. The cytokine inhibitor can be eluted from DEAE using a suitably buffered salt gradient, while in the latter instance the addition of a chaotropic agent may be effective. The salt gradient, as well as the concentration of chaotrope can be determined empirically. Exemplary, however, of an effective salt concentration, wherein the salt is sodium chloride is about 0-0.8 molar.

A third chromatographic technique, that may be used alone or in combination to purify the inhibitor is hydrophobic interaction chromatography. Hydrophobic interaction chromatography is defined as chromatography which affects separation of proteins based on their hydrophobic properties by binding to alkyl groups, attached to a solid surface, such as for example, agarose. The proteins can be differentially eluted from the solid surface with a suitable solvent. If used in combination with other chromatographic techniques, it will generally be employed subsequent to the initial chromatographic steps, such as for example, DEAE chromatography. The materials and methods for utilizing hydrophobic chromatography are described by Shaltiel S., 1984, *Methods in Enzymology*, 104:69. While it is apparent that there are many hydrophobic chromatographic materials and solid supports that may be employed to purify the inhibitor, phenyl Sepharose is particularly effective.

Another chromatographic procedure that may be favorably employed to purify the cytokine inhibitor factor is high performance liquid chromatography, HPLC. HPLC chromatography takes place under high pressure, uses a variety of chromatographic matrices, and thus gives particulary well defined resolution. Examples of the types of materials and methods that can be employed are described by Regnier, F., *Methods in Enzymology* (1983) 91:137. Preferably employed in the subject invention is chromatographic material having phenyl residues. The latter is available commercially from Bio-Rad Corporation, and is sold under the trade name Bio-Gel TSK Phenyl-5-PW. Also, HPLC chromatographic material manufactured by DuPont corporation may be employed, preferably GF250XL for size-exclusion chromatography.

In addition to the above described chromatographic techniques, it will be apparent that size-exclusion chromatography, which effects separation of proteins by excluding structures of a predefined size from the chromatographic material employed, while the chromatographic material retains structures of lesser size, may also be employed in the instant invention. Chromatographic materials used to construct exclusion columns are widely available and sold under numerous trade names, such as the various Sephadexes sold by Pharmacia Corporation. For substantial purification of the inhibitor, size exclusion chromatography is combined with anion exchange chromatography, preferably DEAE chromatography.

In addition to the above described chromatographic methods, a further method, chromatofocusing may be employed. This technique is described in Pharmacia's "FPLC Ion Exchange and Chromatofocusing—Principles and Methods" (1985), and involves eluting proteins off a suitable chromatographic substrate as a function of pH.

Using the above described purification methods, and preferably DEAE, size exclusion chromatography, and/or chromatofocusing, the cytokine inhibitor may be isolated from a suitable biological some and shown to have an apparent molecular weight of about 15–16.4 kD, and about 28–32 kD by SDS PAGE under reducing and non-reducing conditions, respectively. This material would have medical applications, as discussed below, for the treatment of diseases wherein the control of undesirable cytokine levels is the goal.

III. Therapeutic/Prophylactic Applications of Cytokine Inhibitor

The beneficial effect of the cytokine inhibitor can be demonstrated in one of several animal model systems. The preferred animal model system is baboon, and is described by Taylor, et al., 1987, *J. of Clinical Inv.*, 79:918, and by Taylor, et al., 1988, *Circulatory Shock*, 26:227. A baboons response to bacterial exposure that causes sepsis is similar to that displayed by humans, as is the manner of response to therapeutic/prophylactic treatment. Thus, the efficacy of a particular treatment in baboons is generally recognized by those skilled in the art as predictive of a humans response.

Briefly, testing the effectiveness of the inhibitor in the baboon system consists of infusing a lethal dose of *E. Coli*, about $4 \times 10^{10}$ organisms per kilogram of body weight administered over a 2-hour period, before, simultaneous with, or after administration of the inhibitor. This dose of *E. coli* is sufficient to kill 100% of the test animals in a period ranging from 16–32 hours. The animals are anesthetized with sodium pentobarbital in the cephalic vein through a percutaneous catheter. They are also orally intubated and positioned on their right side on a heating pad. Blood samples are removed from the femoral vein which is aseptically cannulated in the hind limb. The percutaneous catheter is used to infuse the *E. coli* organisms. To follow the course of treatment, blood samples are taken at desired time intervals and assayed for white blood cells hematocrit, platelet levels, and fibrinogen. Additionally, mean systemic arterial pressure (MSAP) may be monitored with a transducer (Stratham P2306, Porter) pressure gauge. Changes in these parameters may be prognostic of a patients ability to withstand exposure to a lethal dose of bacteria.

One embodiment of the invention is the administration of an effective amount of the subject cytokine inhibitor to individuals that are at a high risk of developing sepsis, or that have developed sepsis. An example of the former category are patients about to undergo surgery. While the mode of administration is not particularly important, parenteral administration is preferred because of the rapid progression of sepsis, and thus, the need to have the inhibitor disseminate quickly throughout the body. Thus, the preferred mode of administration is to deliver an I.V. bolus slightly before, during, or after surgery. The dosage of the inhibitor will normally be determined by the prescribing physician. It is to be expected that the dosage will vary according to the age, weight and response of the individual patient. Typically, the amount of inhibitor administered per dose will be in the range of about 0.1 to 25 mg/kg of body weight, with the preferred dose being about 0.1 to 10 mg/kg of patient body weight. For parenteral administration, the inhibitor will be formulated in an injectable form combined with a pharmaceutically acceptable parenteral vehicle. Such vehicles are well known in the art and examples include water, saline, Ringer's solution, dextrose solution, and solutions consisting of small amounts of the human serum albumin. The vehicle may contain minor amounts of additives that maintain the isotonicity and stability of the inhibitor. The preparation of such solutions is within the skill of the art. Typically, the cytokine inhibitor will be formulated in such vehicles at a concentration of about 2–8.0 mg/ml to about 100 mg/ml.

Although any similar or equivalent methods and materials may be employed in the practice or testing of the present invention, the preferred methods and materials are now described. The following examples are illustrative of this invention. They are not intended to be limiting upon the scope thereof.

EXAMPLE I

Identification of the Cytokine Inhibitor

Cytokine inhibitor activity was assayed in A375 conditioned media using either the B9 cell IL-6 dependent proliferation assay described by Helle, et al., 1988, *Eur. J. Immunol.*, 18:1535, or by inhibition of IL-6 induced haptoglobin release from HepG2 cells, essentially as described by Castell, 1989, *FEBS*, 242(2):237.

Briefly, HepG2 cells were plated in 96-well culture plates at a density of $3 \times 10^4$ per well and cultured for 2 days, or until confluent, in Iscove's media supplemented with 10% heat inactivated fetal bovine serum, plus glutamine and the standard amount of antibiotics. At the end of the 2 day period, the media removed, HepG2 cells washed with 100 µl of fresh media, and incubated with fresh media, with or without 10 units/ml of human recombinant IL-6 obtained from Amgen Corporation, and with or without different amounts of conditioned media containing cytokine inhibitor from A375 cells. The total volume was 120 µl, and the plates were incubated for 18 hours at 37° C., after which 30 µl was removed and combined with 90 µl of ELISA buffer consisting of 0.05M $NaHCO_3$, pH 9.6. Next, 100 µl of this mixture was removed and assayed by ELISA as described below. The reagents used in the ELISA assay are known to those skilled in the art and readily available. Rabbit and goat anti-haptoglobin antibody are readily available from Sigma Chemical Corporation, as is human haptoglobin, and O-phenylenediamine.

Haptoglobin release was measured by ELISA assay as follows. Nunc immunoplates were pre-coated with 100 µl of a 1:300 dilution of rabbit anti-haptoglobin antibody. The procedure was conducted at 4° C. and the plates were allowed to incubate overnight. The following morning the plates were washed three times with an ELISA wash solution consisting of PBS, pH 7.4, 0.05% Tween-20, and 0.1% thimerosal. The plates were then blocked with 300 µl of block solution consisting of 1% BSA and ELISA buffer. ELISA buffer consisted of 0.05M $NaHCO_3$, pH 9.6. The blocking reaction was conducted for 1 hour at 37° C. The blocking solution and residual BSA were removed by washing the plates an additional 3 times. Next, haptoglobin containing HepG2 supernatants were added to the Nunc immunoplates, and the plates incubated for 1 hour at 37° C. to permit binding of haptoglobin to the haptoglobin antibody bound to the plate. Following the incubation period, the plates were washed 3 times and 100 µl of a 1:1000 dilution of goat anti-human haptoglobin antibody was added and incubated for 30 minutes to 1 hour at 37° C. After the incubation period, the plates were washed 3 times, and a 1:5000 dilution of horseradish peroxidase-antibody conjugate was added and incubated for 30 minutes to 1 hour at 37° C. The HRP-antibody conjugate consisted of swine anti-goat IgG. After the incubation period, the plates were washed an additional 3 times, and the presence of haptoglobin revealed by adding 100 µl of a solution containing 1–30 mg tablet of o-phenylenediamine in 50 ml citrate buffer, plus 20 µl of 30% $H_2O_2$. The reaction was allowed to proceed for 10–20 minutes at room temperature, and stopped by adding 100 μl of 2N $H_2SO_4$. The optical density of the solution was recorded at 490 nm.

Figure 1:
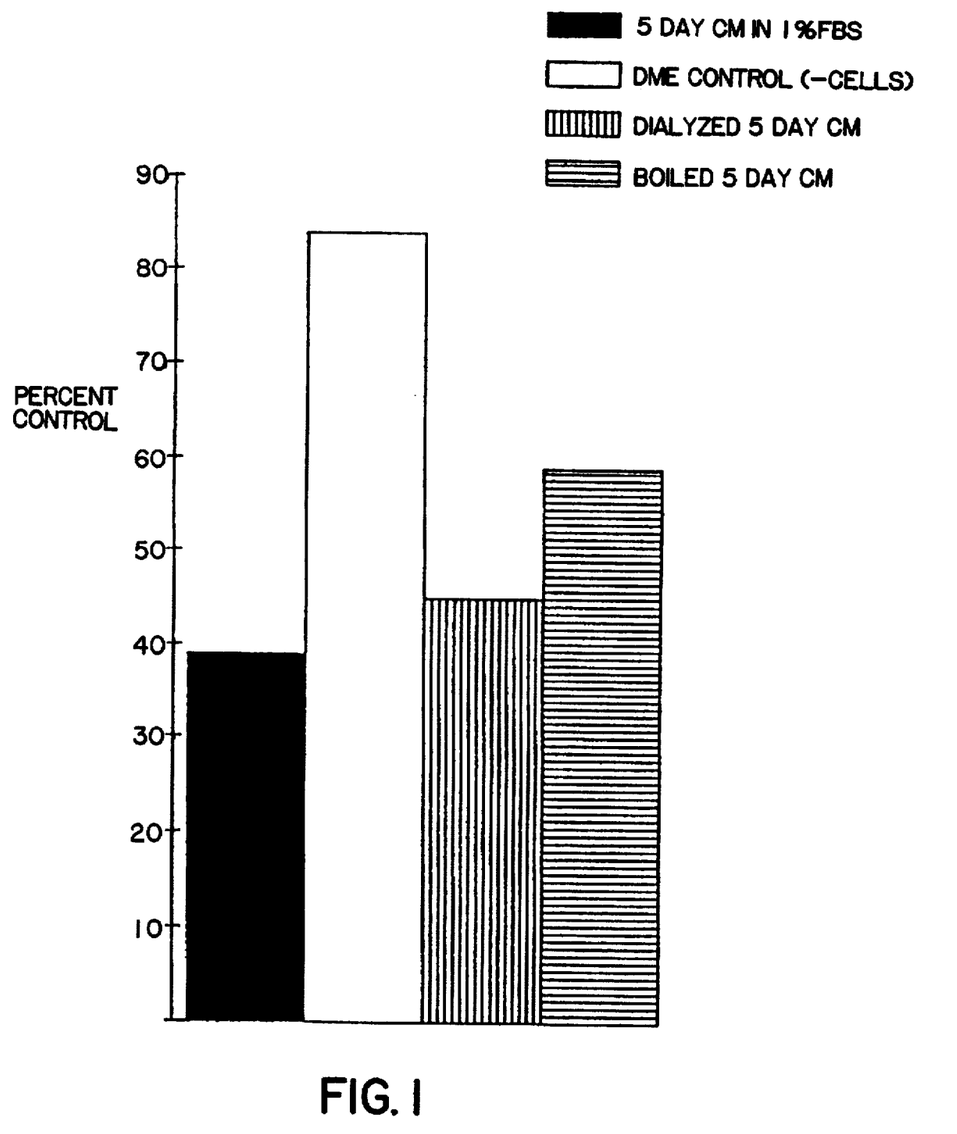
FIG. 1 is a graph depicting the results of bioassays of the cytokine inhibitor present in A375 culture supernatant. Inhibitory activity is measured by the ability of the material to inhibit IL-6-induced haptoglobin release from HepG2 cells.

FIG. 1 shows that the cytokine inhibitor material present in the condition media shows a significant inhibition, about 39%, of IL-6 induced haptoglobin release compared to the IL-6 control.

The results obtained from the HepG2 haptoglobin assay were confirmed using the B9 cell assay system. B9 cells were seeded at a density of either $2\times10^3$ or $5\times10^5$ per microtiter well in the presence or absence of 0.02 units/ml of human recombinant IL-6, and with or without cytokine inhibitor present in the form of A375 conditioned media. The cultures were grown for 3 days, or 4 days, if the cells were seeded at $5\times10^5$ or $2\times10^3$, respectively. B9 cell proliferation was measured by adding 2 μCi/per well of [3H] thymidine and incubating the cells for 4 hours at 37° C., after which the cells were washed, harvested, and counted using standards. It was shown that cells grown in the absence of IL-6 exhibit little or no growth, thus confirming that B9 cell growth is IL-6 dependent.

Figure 2:
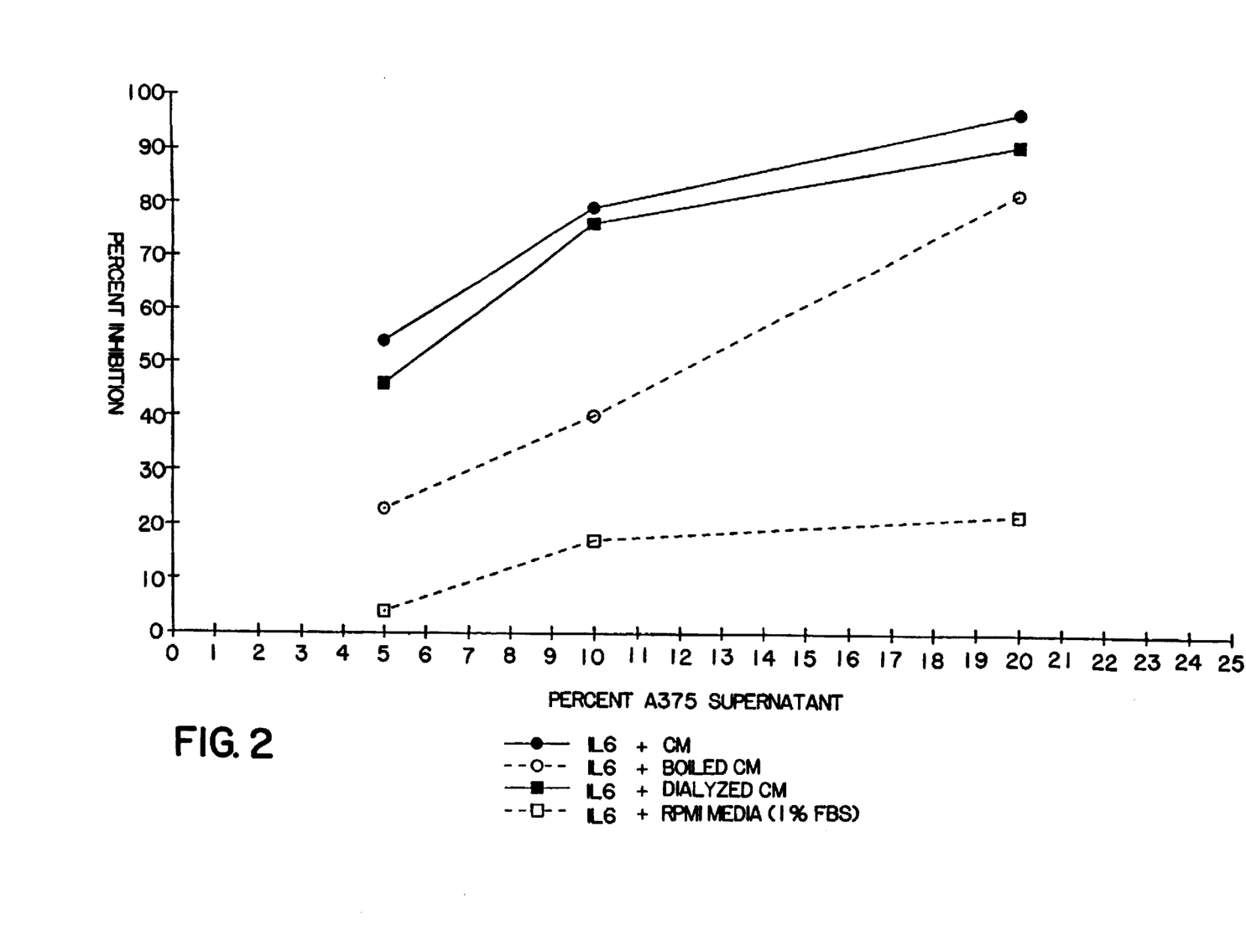
FIGS. 2 and 3 are graphs that depict the inhibitory effect of varying amounts of the cytokine inhibitor present in fluid samples taken from A375 cells on IL-6-dependent B9 cell proliferation. Cell proliferation was measured using a standard [3H] thymidine incorporation assay.
Figure 3:
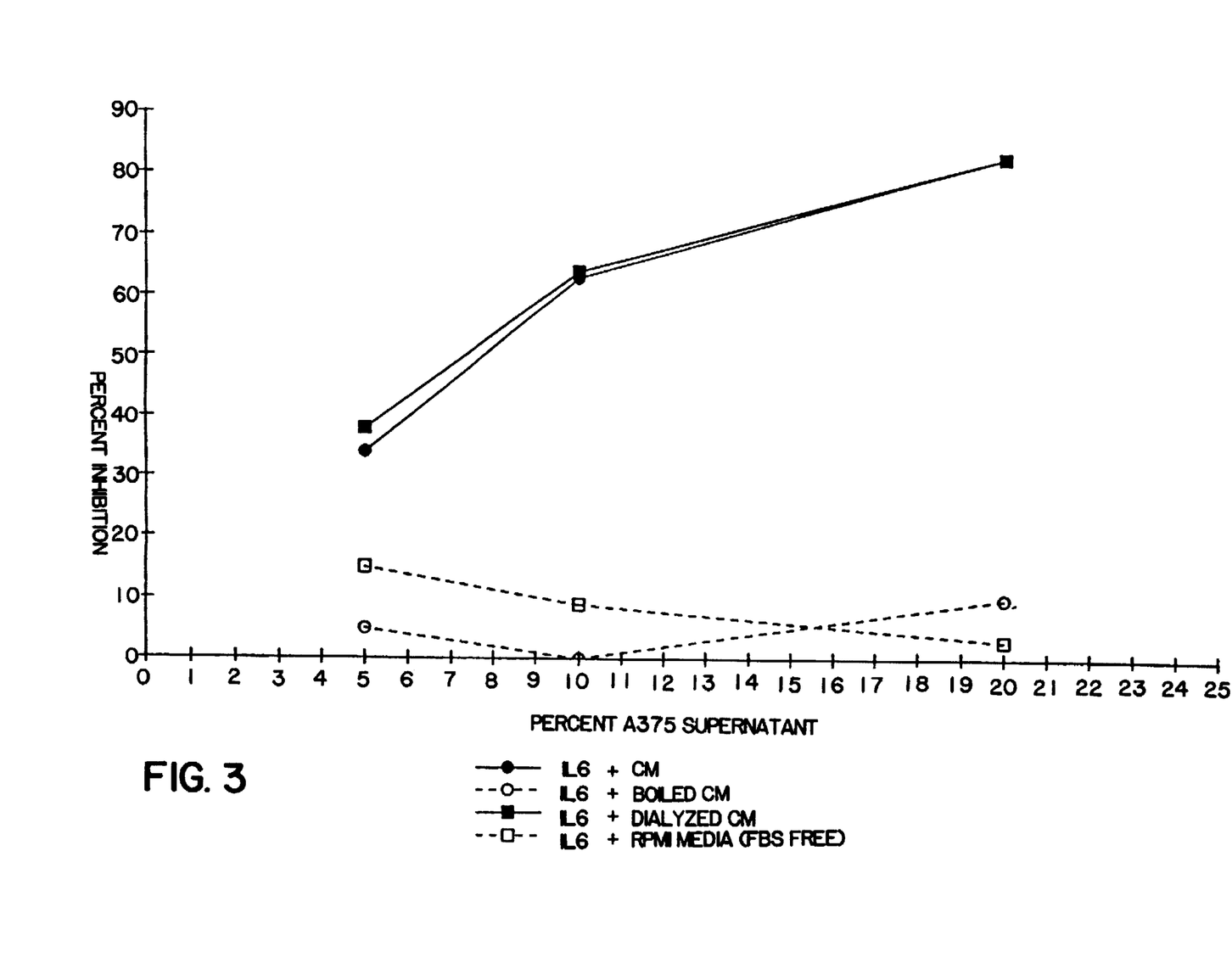
Figure 4:
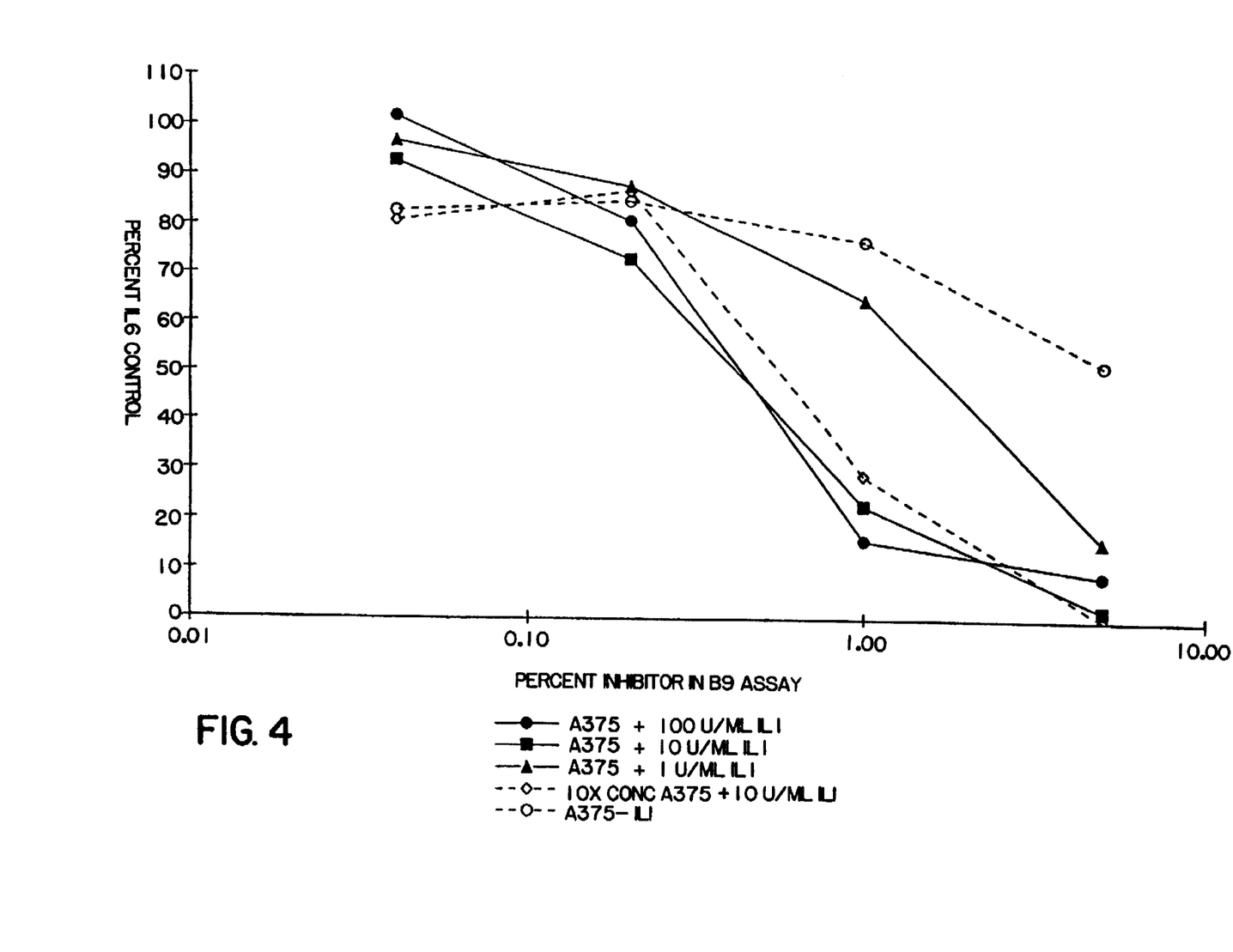
FIG. 4 is a graph depicting the increase in cytokine inhibitor activity in cell culture media from A375 cells as a function of IL-1 concentration.

FIGS. 2 and 3 show that for increasing amounts of conditioned media from A375 cells, there is a corresponding increase in the percent inhibition of IL-6 dependent B9 cell proliferation. Further, FIG. 2 also shows that dialysis of the inhibitor does not affect its activity, whereas boiling the factor markedly reduces its activity. Further, B9 cells grown in the presence of media containing only IL-6, shows no inhibition of B9 cell proliferation.

The above results show that a cytokine inhibitor is present in conditioned media derived from the cell line A375, but is not secreted by the other cell lines tested and shown in Table 1. The inhibitor material present in the condition media was purified and further characterized as to its inhibitory activity, as described below.

EXAMPLE II

Purification of Cytokine Inhibitor

For production of the cytokine inhibitor, A375 cells were grown to confluency in roller bottles using Iscove's media plus 10% FBS at 37° C. Cells were washed with PBS and induced to increase the production of the inhibitor in serum free RPMI 1640 by supplementing it with 10 U/ml IL-1. After three days, the media was collected, spun at 5000 rpm to remove cell debris, frozen, and stored at -20° C. until the purification was to begin.

Figure 5A:
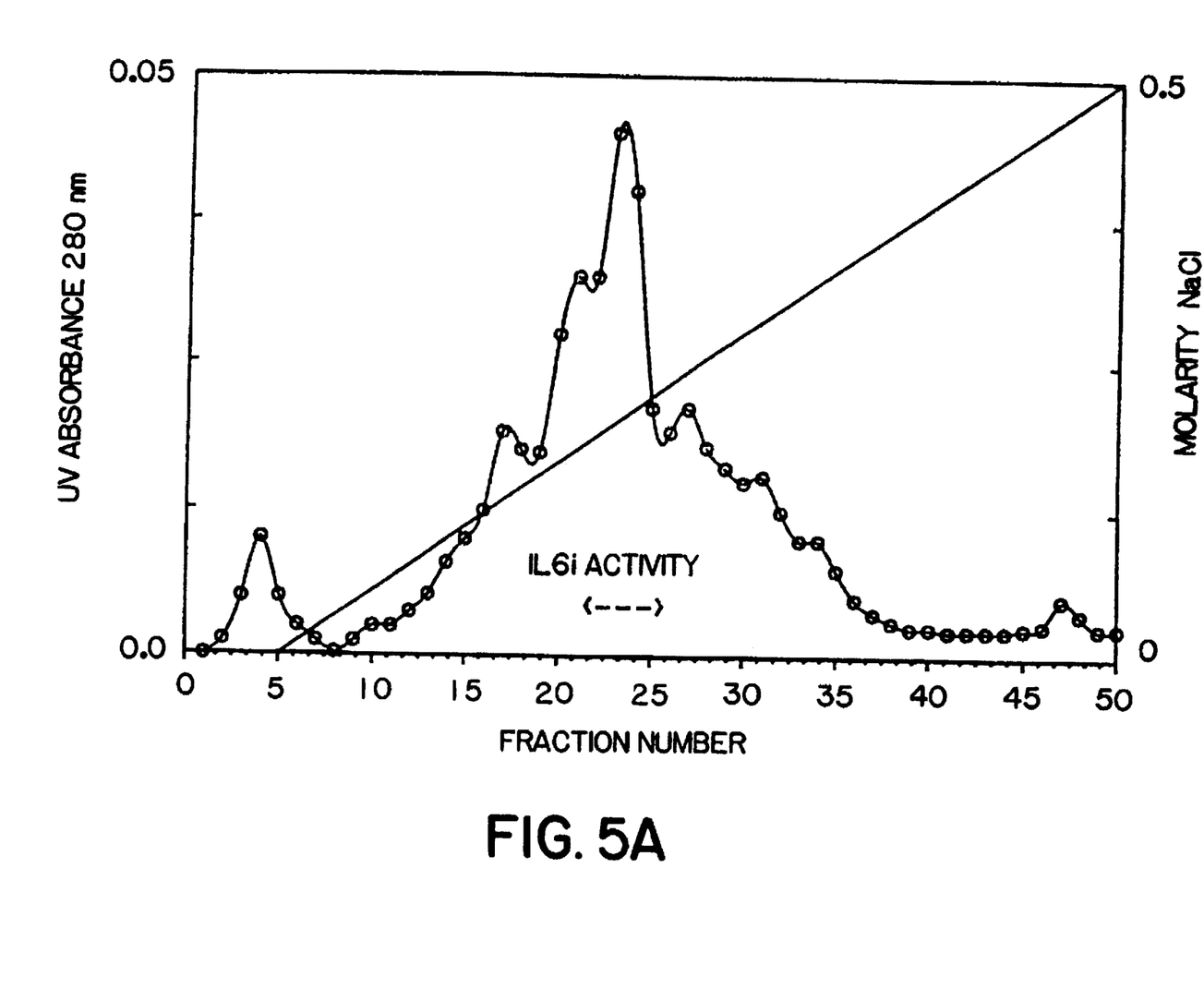
FIG. 5 is a graph depicting diethylaminoethyl chromatographic fractionation of the cytokine inhibitor present in A375 cell conditioned media. Activity was measured as a function of the inhibition of IL-6-dependent B9 cell proliferation.
Figure 5B:
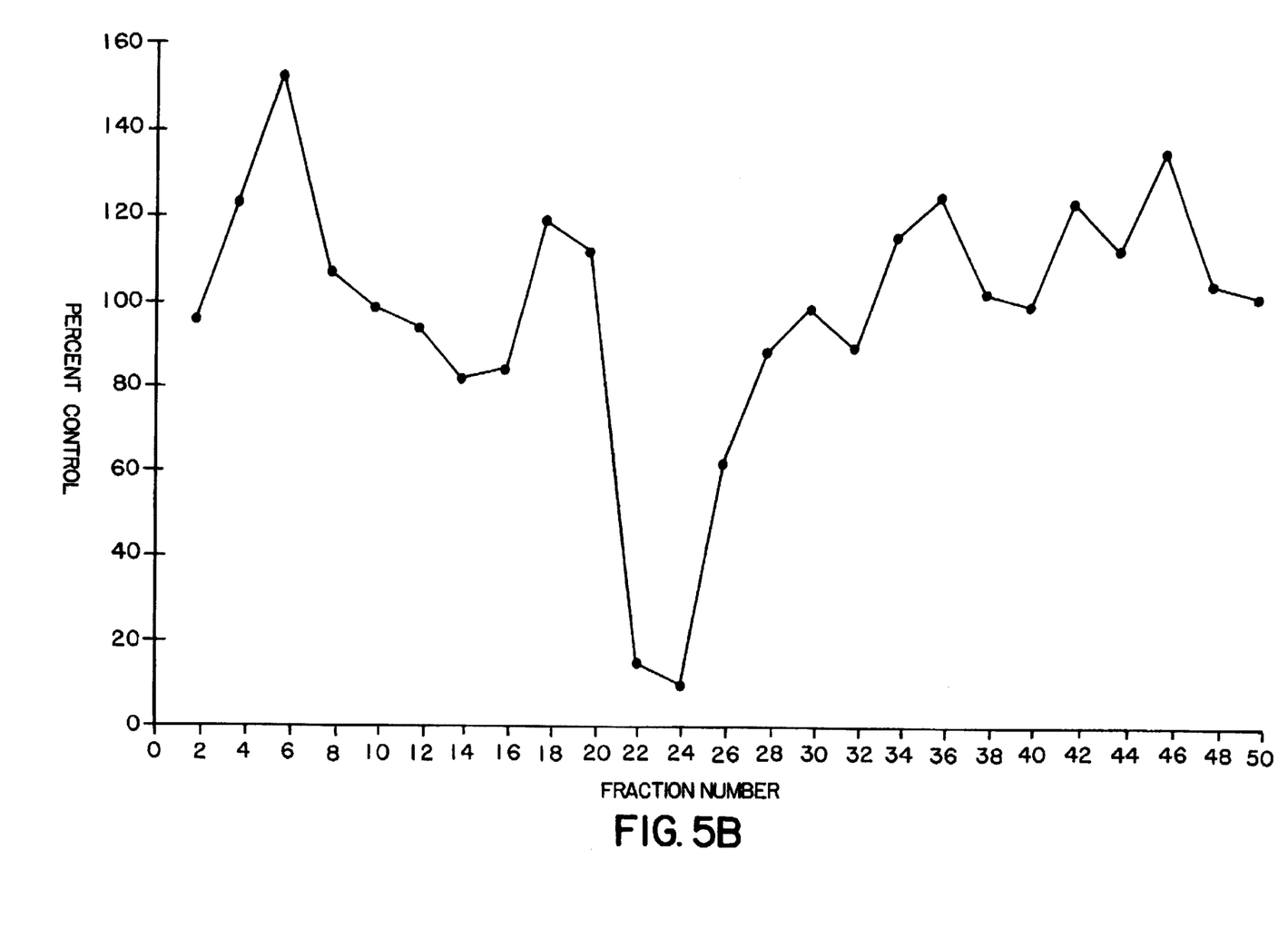

Pooled conditioned medium was thawed, made 0.5 mM in PMSF, and concentrated 10-fold using Amicon stir-cells and 5,000 MWCO membranes. This and most subsequent steps were performed at 4° C. The concentrated sample was dialyzed against a 10× volume of 10 mM Tris-Cl, pH 8.0, 0.001% in Tween 80. The dialyzed sample was pumped through a 50×100 mm column of DEAE-Sepharose (HR, Fast-Flow) to bind the cytokine inhibitor. Unbound proteins were removed by washing the column with dialysis buffer, and bound proteins were eluted with a salt gradient (0–0.5M NaCl in dialysis buffer). Elution of protein was followed by monitoring absorbance at 280 nm. Fractions were collected and assayed for inhibitory activity using the B-9 assay. The results are shown in FIG. 5. Cytokine inhibitory activity elutes at a salt concentration of about 0.17–0.25 NaCl, which corresponds to fractions 21–27.

Figure 6A:
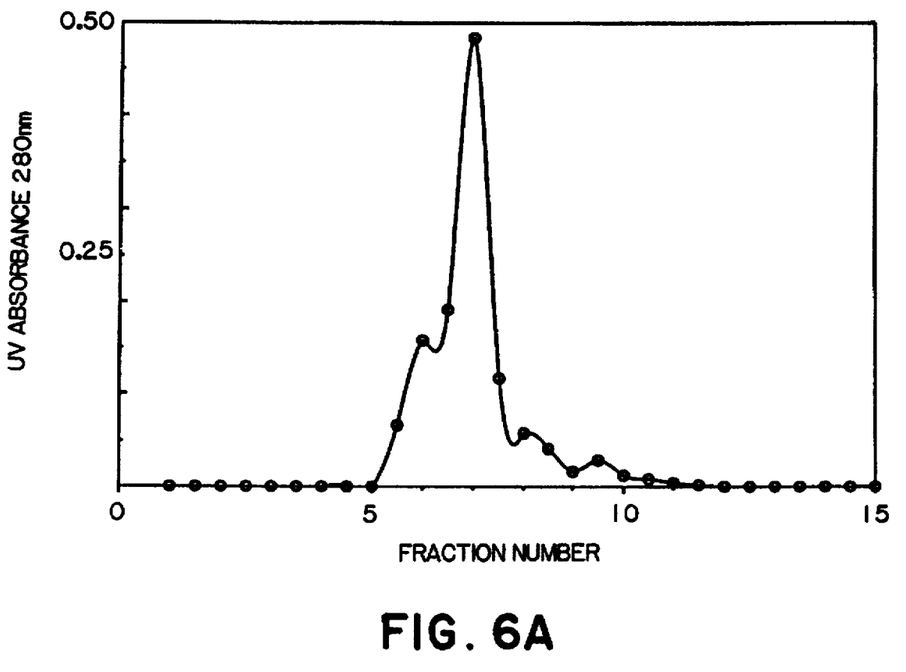
FIG. 6 is a graph depicting GF-250XL chromatography of the 0.25M NaCl eluate from the diethylaminoethyl chromatography in FIG. 5. The 0.25M eluate was concentrated using an ultrafilter fitted with a YM10 membrane and then chromatographed on the GF-250 column. Maximum cytokine inhibitory activity was present in fraction 9 as ascertained by the ability of this fraction to inhibit IL-6-dependent B9 cell proliferation.
Figure 6B:
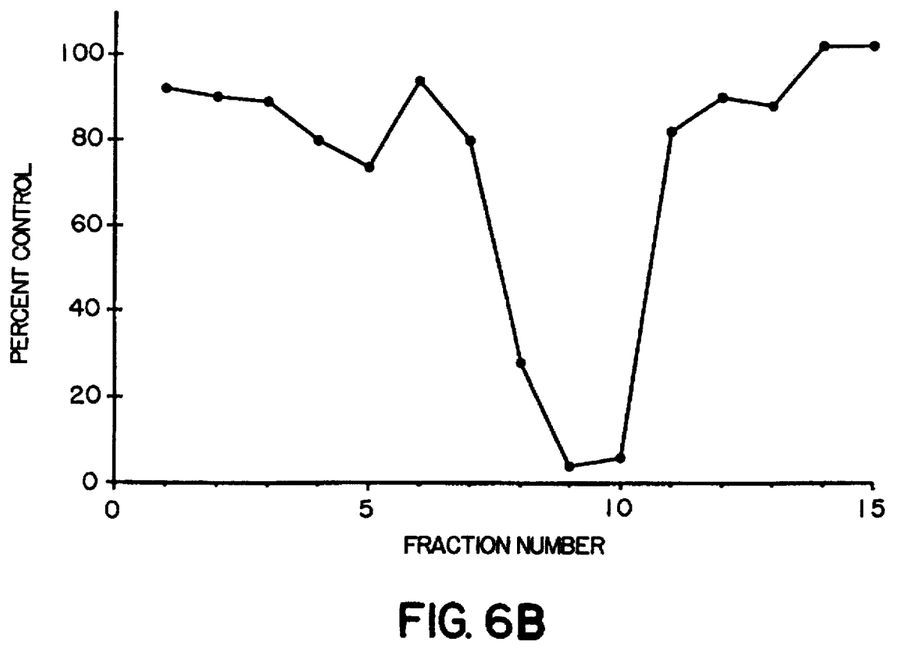
Figure 9:
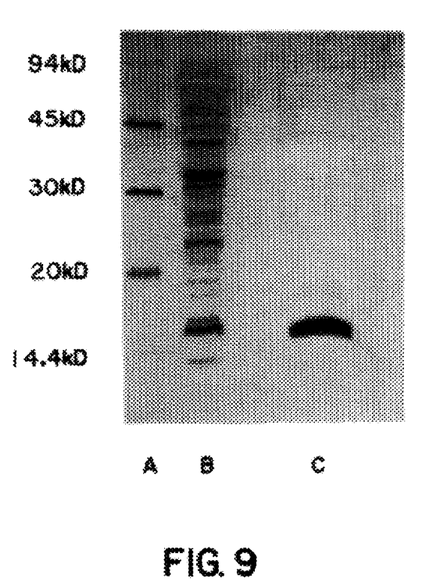
FIG. 9 shows an SDS-PAGE silver stained gel comparing the cytokine inhibitor purified by chromatofocusing, lane c; eluate from the GF-250XL column that was added to the chromatofocusing column, lane b; and molecular weight standards, lane a. The standards were phosphorylase B (94 kD), BSA (67 kD), ovalbumin (45 kD), carbonic anhydrase (30 kD), soybean trypsin inhibitor (20 kD),and alpha lactalbumin (14.4 kD). The standards were obtained from Pharmacia.

The peak of inhibitory activity from the DEAE chromatography step was pooled, concentrated to 2–3 ml using an Amicon stir-cell, and further purified using HPLC size-exclusion chromatography. A 1 ml sample was injected onto a DuPont GF250XL column previously equilibrated with PBS. The sizing column flow rate was 3 ml/min. Resolved proteins were detected by monitoring UV absorbance at 280 nm. Fractions were collected and assayed for cytokine inhibitory activity using the B9 cell assay. FIG. 6 shows that most of the inhibitory activity is found in fractions 7–10. Based on the elution volume of the inhibitory activity from the sizing column, the cytokine inhibitor was calculated to have an approximate molecular weight of 20 kD. Inspection of silver-stained bands on the reducing SDS-PAGE gel covering the active fractions shows several prominent bands in the 10–25 kD region. See FIG. 9, lane b.

Figure 7A:
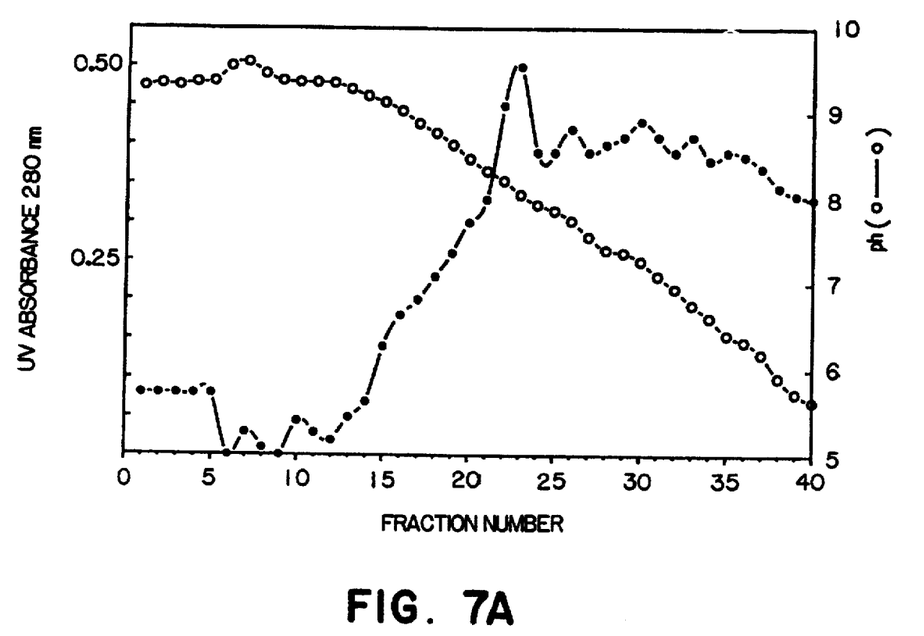
FIG. 7 shows the results of chromatofocusing the eluate from the GF-250XL column described in FIG. 6. Maximum cytokine inhibitory activity was present in fraction 23 as ascertained by the ability of this fraction to inhibit IL-6-dependent B9 cell proliferation.
Figure 7B:
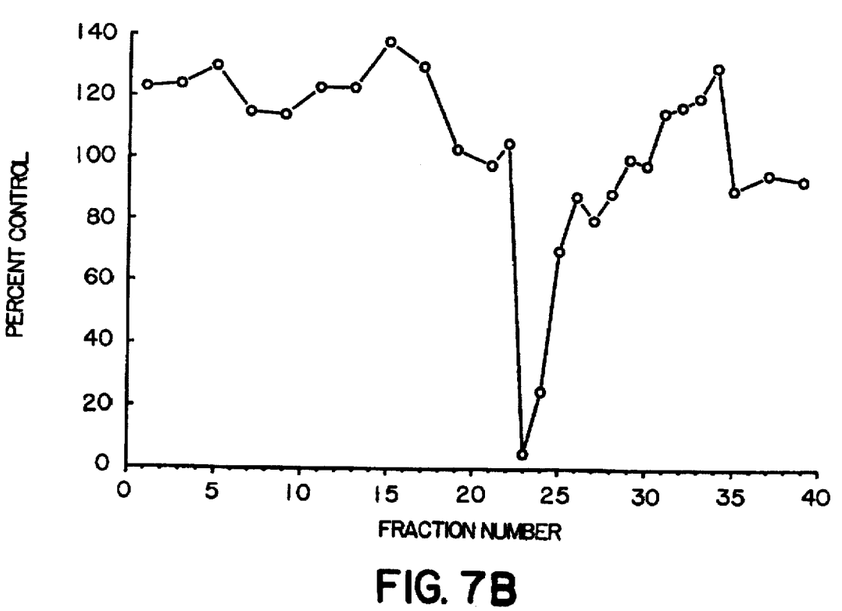

The fractions containing the peak of cytokine inhibitory activity from the sizing chromatography step were pooled, concentrated to 1–2 ml, and diafiltered using 25 mM imidazole-HCl, pH 7.4. Diafiltered inhibitor was injected onto a Mono P chromatofocusing column (1×20 cm) and proteins were resolved by generating a pH elution gradient using 10% Polybuffer 94 adjusted to pH 4.0. The flow rate was 1 ml/min. Elution of proteins was followed by monitoring absorbance at 280 nm. Fractions were collected and assayed for cytokine inhibitory activity using the B9 cell proliferation assay. At this step in the purification the majority of the contaminating protein is serum albumin. Albumin elutes late in the pH gradient (approximately pH 4.6). The cytokine inhibitor elutes early in the pH gradient, at approximately pH 8.0. See FIG. 7.

Figure 8:
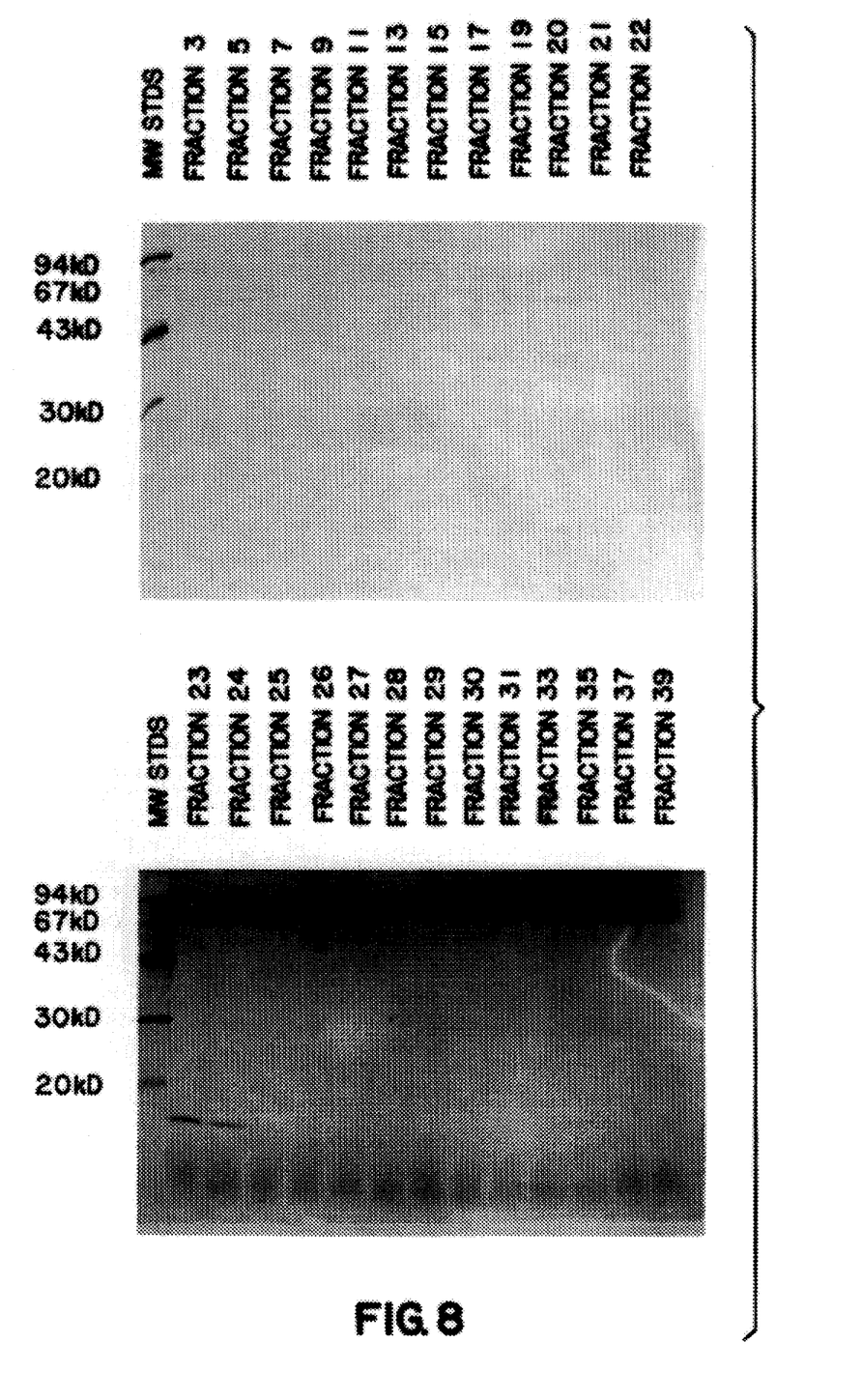
FIG. 8 shows SDS-PAGE analysis of the cytokine inhibitor purified by chromatofocusing. 12% polyacrylamide gels were run. Protein was detected by silver staining.
Figure 10:
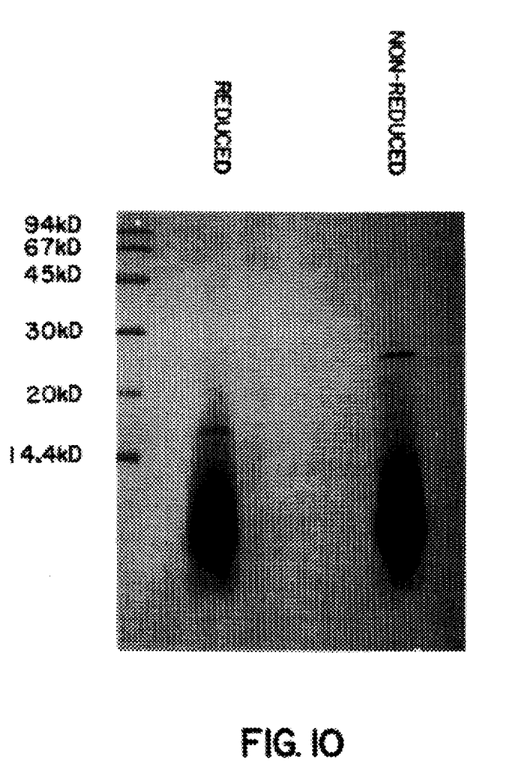
FIG. 10 shows an SDS-PAGE silver stained gel comparing reduced (A) and non-reduced (B) cytokine inhibitor. The standards were phosphorylase B (94 kD), BSA (67 kD), ovalbumin (45 kD), carbonic anhydrase (30 kD), soybean trypsin inhibitor (20 kD),and alpha lactalbumin (14.4 kD).

SDS-PAGE analysis of the protein components in the fractions collected across the column shows a single major protein band in the region of the inhibitory bioactivity. See FIG. 8. The protein in that band has an apparent molecular weight on a reducing SDS polyacrylamide gel of about 15.4 kD. See FIG. 8, and FIG. 9, lane c. In a subsequent experiment the protein was shown to have a molecular weight of about 16.4 under reducing conditions. (FIG. 10) The protein has a mobility of about 28–30 kD on a non-reducing gel.

Samples from each step of the purification were analyzed for purity by SDS-PAGE. Resolved proteins in the gels were detected either by staining with Coomassie Blue or by silver staining (ICN Rapid-Ag-Stain Kit).

Based on Coomassie Brilliant Blue staining of the 15.4 kD band on a gel, it was estimated that the purification protocol described above will yield approximately 40 μg of purified cytokine inhibitor from 4 liters of A375 conditioned medium. Using purified inhibitor, we have defined a unit of cytokine inhibitory activity as that amount that will give 50% inhibition of 1 pg/ml of IL-6.

Automated sequence analysis of the 15.4 kd protein was conducted on an Applied Biosystems 470A gas-phase sequencer as is known in the art. A partial amino terminal sequence was obtained and consists of $H_2N$-Glycine-Leucine-Glutamic acid. A more detailed analysis gave the following sequence: $H_2N$-Gly-Leu-Glu-X-Asp-Gly-Lys-Val-Asn-Ile-X-X-Lys-Lys-Gln-Phe-Phe-Val-Ser-Phe-Lys-Asp-Ile-Gly-Trp-Asn-Asp-Trp-Ile.

The "X" corresponds to amino acids that were not positively identified but are most likely cysteine.

EXAMPLE III

Properties of Cytokine Inhibitor

A. Purification Cytokine Inhibitor is a Protein

To confirm that the inhibitor is a protein, it was treated with a protease, trypsin, to determine to what extent the activity is sensitive to trypsin cleavage. Table 2 shows the results wherein the B9 proliferation assay was used to measure activity. The control showed that IL-6 alone exhibits significant B9 cell proliferation, whereas IL-6 plus the inhibitor material at either 0.5% or 5% significantly inhibits or completely inhibits, respectively, IL-6 dependent B9 cell proliferation. Further shown in Table 2 is that when the 0.5% or 5% solution of IL-6 inhibitor is treated with trypsin, the material no longer inhibits the effects of IL-6. This establishes that the cytokine inhibitory activity is destroyed by trypsinization.

The experiment was run by pre-treating 100 μg of fraction number 9 containing 10 μg of TPCK-treated trypsin. The reaction was conducted in Tris buffered saline (TBS), and the mixture incubated for 60 minutes at 37° C. This experiment was repeated, and Table 2 shows that trypsin treatment causes a complete loss of cytokine inhibitor activity.

TABLE 2

| Treatment | | CPM ($^3$H-Thymidine Incorp.) |
|---|---|---|
| IL-6 2 pg/ml | | 11927 ± 617 |
| IL-6 + #9 | .5% | 6954 ± 640 |
| | .5% | 143 ± 19 |
| IL-6 + trypsin-treated | .5% | 11366 ± 922 |
| #9 | .5% | 11916 ± 567 |
| IL-6 2 pg/ml | | 7902 ± 345 |
| IL-6 + trypsin | .5% | 8028 ± 461 |
| | 5% | 8455 ± 731 |

Additional characterization of the inhibitor was done. Inhibitor activity is not effected by dialysis, but is reduced by boiling.

B. IL-6 Inhibitor Competes With Human IL-6

An experiment was performed to determine whether the inhibitor present in fraction 9 above competes with IL-6 in the B9 IL-6 dependent cell proliferation assay. [$^3$H] thymidine was used to assess B9 cell IL-6 dependent proliferation. Human recombinant IL-6 (Amgen) was used at a concentration ranging from 2 pg/ml to 500 pg/ml. Table 3 shows the results observed when the inhibitor is present at a concentration of 0.05% and 0.5%. It is apparent that increasing the IL-6 concentration over this range completely blocks the activity of the IL-6 inhibitor when present at a 0.5% dilution and further shows significant blockage of activity at 0.5% dilution.

TABLE 3

| | CPM | | |
|---|---|---|---|
| IL-6 | No. Inhibitor | .05% Inhibitor | 0.50% Inhibitor |
| 2 pg/ml | 10150 ± 1259 | 4963 ± 342 | 55 ± 10 |
| 20 pg/ml | 11423 ± 884 | 9520 ± 793 | 1833 ± 220 |
| 100 pg/ml | 10546 ± 1315 | 9794 ± 1358 | 3343 ± 87 |
| 500 pg/ml | 6639 ± 275 | 6779 ± 458 | 3856 ± 197 |

EXAMPLE IV

Therapeutic/Prophylactic Applications of the Cytokine Inhibitor

Sepsis

The effectiveness of the cytokine inhibitor in a baboon sepsis model system is tested essentially as described by Taylor, et al., 1987, *J. of Clinical Inv.*, 79:918, and by Taylor, et al., 1988, *Circulatory Shock*, 26:227. Briefly, this consists of first measuring IL-6 levels in baboon plasma in response to a lethal or sublethal dose of *E. coli.*, and secondly, determining if the inhibitor is effective in treating sepsis by preventing the death, or prolonging the lives of septic animals. A lethal or sublethal dose of *E. coli* consist of approximately $4 \times 10^{10}$ and $0.4 \times 10^{10}$ organisms, respectively.

After administration of a lethal dose of *E. coli*, IL-6 levels start to increase after 1 hour, at which time it is about 1,500 pg/ml, and continue to increase for at least up to 6 hours to about 9,000 pg/ml. In contrast, there is little perceptible increase in IL-6 after administration of a sublethal dose of *E. coli*. Baboons that receive a lethal dose of *E. coli* invariably die within 16–32 hours. Taylor, et al., 1987, *J. of Clinical Inv.*, 79:918, and Taylor, et al., 1988, *Circulatory Shock*, 26:227.

The effectiveness of the cytokine inhibitor in preventing the death or prolonging the lives of baboons is tested using two administration routines wherein the inhibitor is delivered in physiological saline. In the first, 6.0 mg of inhibitor per kg of body weight is administered in three separate doses at 24, 22, and 21 hours before a lethal challenge of bacteria. Alternatively, 5.0 mg of inhibitor per kg of body weight is administered in a single dose simultaneously with the bacterial challenge. In both instances the inhibitor considerably extends the lifetime of the baboons that receive the multiple or single dose treatment and survive well beyond 48 hours. Recall that baboons that receive a lethal dose of *E. coli* invariably die within 16–32 hours.

Cancer

IL-6 is an autocrine growth factor for renal cell carcinomas. Miki, S., et al., 1989, *FEBS* 250:607–610. Thus, the cytokine inhibitor would interfere with the autocrine activity of IL-6 and be an effective chemotherapeutic for the treatment of this form of cancer. The inhibitor can be administered in an effective amount, with the dosage of the inhibitor normally being determined by the prescribing physician. It is to be expected that the dosage will vary according to the tumor mass, as well as the age, weight, and response of the individual patient. Typically, the amount of inhibitor administered per dose will be in the range of about 0.1 to 25 mg/kg of body weight, with the preferred dose being about 0.1 to 10 mg/kg of patient body weight. For parenteral administration, the inhibitor will be formulated in an injectable form combined with a pharmaceutically acceptable parenteral vehicle. Such vehicles are well known in the art and examples include water, saline, Ringer's solution, dextrose solution, and solutions consisting of small amounts of the human serum albumin. The vehicle may contain minor amounts of additives that maintain the isotonicity and stability of the inhibitor. The preparation of such solutions is within the skill of the art. Typically, the cytokine inhibitor will be formulated in such vehicles at a concentration of about 2–8.0 mg/ml to about 100 mg/ml.

EXAMPLE V

Inhibitory Activity of Molecules that Comprise the Inhibitor

As discussed above, a comparison of the amino acid sequence of the IL-6 inhibitor to sequences of known proteins in a computerized protein data base revealed that the inhibitor has the amino terminal sequence of the $\beta_A$ chain of at least two proteins and includes inhibin A, and activin.

Experiments can be performed to show that these molecules, and preferably activin, have IL-6 inhibitor activity as ascribed to the inhibitor of the instant invention.

Specifically, the cytokine inhibitory activity may be shown using either the B9 cell IL-6 dependent proliferation assay, or the inhibition of IL-6 induced haptoglobin release assay from HepG2 cells, essentially as described above.

Briefly, HepG2 cells would be plated in 96-well culture plates at a density of $3 \times 10^4$ per well and cultured for 2 days, or until confluent, in Iscove's media supplemented with 10% heat inactivated fetal bovine serum, plus glutamine and the standard amount of antibiotics. At the end of the 2 day period, the media is removed, HepG2 cells are washed with 100 µl of fresh media, and incubated with fresh media, with or without 10 units/ml of human recombinant IL-6 obtained from Amgen Corporation, and with or without different amounts of activin. The total volume is 120 µl, and the plates are incubated for 18 hours at 37° C., after which 30 µl is removed and combined with 90 µl of ELISA buffer consisting of 0.05M $NaHCO_3$, pH 9.6. Next, 100 µl of this mixture is removed and assayed by ELISA as described below. The ELISA assay is known to those skilled in the art and readily available. Rabbit and goat anti-haptoglobin antibody are available from Sigma Chemical Corporation, as is human haptoglobin, and O-phenylenediamine.

Haptoglobin release is measured by ELISA assay as follows. Nunc immunoplates are pre-coated with 100 µl of a 1:300 dilution of rabbit anti-haptoglobin antibody. The procedure is conducted at 4° C. and the plates are allowed to incubate overnight. The following morning the plates are washed three times with an ELISA wash solution consisting of PBS, pH 7.4, 0.05% Tween-20, and 0.1% thimerosal. The plates are then blocked with 300 µl of block solution consisting of 1% BSA and ELISA buffer. ELISA buffer consists of 0.05M $NaHCO_3$, pH 9.6. The blocking reaction is conducted for 1 hour at 37° C. The blocking solution and residual BSA are removed by washing the plates an additional 3 times. Next, haptoglobin containing HepG2 supernatants are added to the Nunc immunoplates, and the plates incubated for 1 hour at 37° C. to permit binding of haptoglobin to the haptoglobin antibody bound to the plate. Following the incubation period, the plates are washed 3 times and 100 µl of a 1:1000 dilution of goat anti-human haptoglobin antibody is added and incubated for 30 minutes to 1 hour at 37° C. After the incubation period, the plates are washed 3 times, and a 1:5000 dilution of horseradish peroxidase-antibody conjugate is added and incubated for 30 minutes to 1 hour at 37° C. The HRP-antibody conjugate consists of swine anti-goat IgG. After the incubation period, the plates are washed an additional 3 times, and the presence of haptoglobin revealed by adding 100 µl of a solution containing 1–30 mg tablet of o-phenylenediamine in 50 ml citrate buffer, plus 20 µl of 30% $H_2O_2$. The reaction is allowed to proceed for 10–20 minutes at room temperature, and stopped by adding 100 µl of 2N $H_2SO_4$. The optical density of the solution would be recorded at 490 nm.

Data gathered from the above experiment would show that activin exhibits a significant inhibition of IL-6 induced haptoglobin release compared to the IL-6 control.

The results obtained from the HepG2 haptoglobin assay would be confirmed using the B9 cell assay system. B9 cells are seeded at a density of either $2 \times 10^3$ or $5 \times 10^5$ per microtiter well in the presence or absence of 0.02 units/ml of human recombinant IL-6, and with or without activin. The cultures are grown for 3 days, or 4 days, if the cells are seeded at $5 \times 10^5$ or $2 \times 10^3$, respectively. B9 cell proliferation is measured by adding 2 µCi/per well of [3H] thymidine and incubating the cells for 4 hours at 37° C., after which the cells are washed, harvested, and counted using standards.

Based on this assay it would be shown that cells grown in the absence of IL-6 exhibit little or no growth, thus confirming that B9 cell growth is IL-6 dependent, and that for increasing amounts of activin, there is a corresponding increase in the percent inhibition of IL-6 dependent B9 cell proliferation. Further, B9 cells grown in the presence of media containing only IL-6, and no activin would show no inhibition of B9 cell proliferation.

EXAMPLE VI

Use of Activin for the Treatment of Disease

Activin may be beneficially applied as a therapeutic or prophylactic for the treatment of sepsis or cancer. However, the administering physician should take into account that this molecule has recently been shown, or is thought to be involved in gonadal control of follicle-stimulating hormone. Thus, this dictates that the physician empirically determine a suitably effective dose for treating disease that will not have an untoward effect on the well being of the patient.

The present invention has been described with reference to specific embodiments. However, this application is intended to cover those changes and substitutions which may be made by those skilled in the art without departing from the spirit and the scope of the appended claims.

We claim:

1. A method for identifying melanoma cells that produce a protein inhibitor of cytokine activity, comprising the steps of:
    a) growing melanoma cells in a culture media; and
    b) assaying said culture media for said protein inhibitor.
2. The method of claim 1, wherein said melanoma cells are human.
3. The method of claim 2, wherein said melanoma cells are A375 cells.
4. The method of claim 1, wherein said cytokine activity is IL-6 activity.
5. The method of claim 3, wherein said inhibitor comprises activin.
6. A method of purifying a protein inhibitor of interleukin activity from a solution containing said inhibitor and contaminating proteins, comprising the steps of:
    a) contacting a first fluid solution containing said inhibitor and contaminating proteins with anion exchange chromatographic material to cause said inhibitor and said contaminating proteins to bind to said chromatographic material; and
    b) separating said inhibitor from said contaminating proteins by contacting said chromatographic material with a second solution containing an effective salt concentration.
7. The method as described in claim 6, wherein said anion exchange chromatographic material is diethylaminoethyl sepharose.
8. The method as described in claim 7, wherein said second solution comprises about 0.15–25M NaCl.
9. The method as described in claim 8, wherein said cytokine activity is IL-6 activity.
10. The method as described in claim 8, wherein said inhibitor comprises activin.
11. The method of claim 6, wherein said interleukin is IL-6.

* * * * *